US009995696B2

(12) United States Patent
Himmel

(10) Patent No.: US 9,995,696 B2
(45) Date of Patent: Jun. 12, 2018

(54) OPEN-AIR CRYSTALLIZATION PLATE COOLER

(71) Applicant: Daniel Marc Himmel, Bala Cynwyd, PA (US)

(72) Inventor: Daniel Marc Himmel, Bala Cynwyd, PA (US)

( * ) Notice: Subject to any disclaimer, the term of this patent is extended or adjusted under 35 U.S.C. 154(b) by 0 days. days.

(21) Appl. No.: 15/422,470

(22) Filed: Feb. 2, 2017

(65) Prior Publication Data
US 2017/0299527 A1    Oct. 19, 2017

Related U.S. Application Data

(60) Provisional application No. 62/290,378, filed on Feb. 2, 2016.

(51) Int. Cl.
*G01N 23/20* (2018.01)
*G01N 23/207* (2018.01)

(52) U.S. Cl.
CPC ..... *G01N 23/20008* (2013.01); *G01N 23/207* (2013.01); *G01N 2223/3103* (2013.01)

(58) Field of Classification Search
CPC ........... G01N 23/20008; G01N 23/207; G01N 2223/3103; C30B 11/00; C30B 35/00
USPC ...................... 359/398; 356/36, 246; 117/204
See application file for complete search history.

(56) References Cited

U.S. PATENT DOCUMENTS

| | | | |
|---|---|---|---|
| 2,232,354 A | | 2/1941 | Weygand |
| 3,297,491 A | | 1/1967 | Kolenko |
| 5,181,382 A | * | 1/1993 | Middlebrook ......... G02B 21/28 219/201 |
| 5,257,128 A | * | 10/1993 | Diller ..................... G02B 21/28 359/395 |
| 5,735,129 A | | 4/1998 | Ienaga |
| 6,727,089 B2 | * | 4/2004 | Ho ......................... C12M 41/12 356/244 |

(Continued)

OTHER PUBLICATIONS

Holzinger, A. "Temperature Controlled Microscopy," Modern Research and Educational Topics in Microscopy, Formatex, 2007, pp. 951-955.

(Continued)

*Primary Examiner* — Frank Font
(74) *Attorney, Agent, or Firm* — Mendelsohn Dunleavy, P.C.; Steve Mendelsohn

(57) ABSTRACT

This invention is intended to allow an experimenter to work at amenable temperatures while viewing and/or manipulating aqueous protein crystals or other specimens under a dissection microscope at close to 4° C. or other controlled temperatures. The invention provides a specimen stage chamber large enough to fit a multi-well plate containing the specimens. The temperature of this specimen stage chamber is controlled by transparent coolant circulated through its walls and through a transparent chamber beneath the specimen stage chamber, without blocking the light path of the microscope. An additional chamber cools the air above the specimen stage chamber. In one version of this apparatus, circulation of most coolants is replaced by an array of Peltier coolers. The apparatus is open to the air above, giving the experimenter direct access to the crystals for manipulation. The invention may have wider application for manipulation of other specimens under a microscope.

23 Claims, 9 Drawing Sheets

(56) References Cited

U.S. PATENT DOCUMENTS

| | | | | |
|---|---|---|---|---|
| 7,247,499 B2* | 7/2007 | Schembri | ............... | B01F 9/002 |
| | | | | 435/287.1 |
| 8,277,763 B2 | 10/2012 | Steinmann et al. | | |
| 8,372,358 B2 | 2/2013 | Groisman et al. | | |
| 8,767,293 B2* | 7/2014 | Miteva | ................. | G02B 21/34 |
| | | | | 356/244 |
| 8,859,263 B2* | 10/2014 | Greenberger | .......... | C12M 23/12 |
| | | | | 359/395 |
| 2004/0126876 A1* | 7/2004 | Ravin | .................... | B01L 3/508 |
| | | | | 435/288.3 |
| 2005/0138934 A1 | 6/2005 | Weigert et al. | | |
| 2009/0075360 A1 | 3/2009 | Ho et al. | | |
| 2010/0103512 A1* | 4/2010 | Ranoux | ................. | G01N 21/03 |
| | | | | 359/398 |
| 2010/0284016 A1* | 11/2010 | Teitell | .................... | G01J 3/453 |
| | | | | 356/451 |
| 2012/0009671 A1 | 1/2012 | Hansen et al. | | |
| 2013/0115606 A1 | 5/2013 | Hansen et al. | | |

OTHER PUBLICATIONS

"Live Cell Imaging Handbook & Catalogue," Live Cell Instrument, Feb. 2, 2012, vol. 6-1, 75 pages.

Bolanos-Garcia, Victor M., and Naomi E. Chayen. "New directions in conventional methods of protein crystallization." Progress in biophysics and molecular biology 101.1 (2009): 3-12.

"TG40 User Manual," Centeo Biosciences Ltd., Sep. 2010, pp. 1-40.

* cited by examiner

OPEN-AIR CRYSTALLIZATION PLATE COOLER

CROSS-REFERENCE TO RELATED APPLICATIONS

This application claims the benefit of the filing date of U.S. provisional application No. 62/290,378, filed on Feb. 2, 2016, the teachings of which are incorporated herein by reference in their entirety.

BACKGROUND OF THE INVENTION

Field of the Invention

The present invention relates to microscopes and, more particularly, to apparatuses for holding samples to be viewed using microscopes.

Background

X-ray crystallography uses X-ray diffraction to construct three-dimensional images of molecules, large and small, to atomic or near atomic resolution. The ability to ascertain the shape of a molecule and pinpoint the location of each and every atom in that molecule is revolutionizing such diverse fields as electronics and medicine. To collect X-ray diffraction data for structure determination, a crystal composed of the molecule in question is placed in an X-ray beam, and the resulting X-ray diffraction pattern is recorded for analysis and structure determination. To determine the structure of any chemical species by X-ray crystallography first requires one to grow a highly-ordered crystal composed of that chemical species. Particularly with larger molecules ("macromolecules") grown in aqueous solution, crystallization remains the single largest bottleneck to structure determination, as there is no way at present to predict the conditions under which a highly-ordered crystal will grow. Common conditions to test by trial-and-error include concentration of the macromolecule, concentration of other chemical additives, and solution pH. One important variable for crystallization is temperature. While many macromolecules can be crystallized successfully at room temperature, a very large fraction will only form highly-ordered crystals at lower temperatures such as 4° Celsius. This is especially true with biological molecules such as many proteins.

To prepare a single crystal for data collection often requires meticulous handling under a polarized-light, optical microscope. Under the microscope, multiple crystals may be handled at one sitting in a container called a "crystallization plate" that contains many solution wells. A number of crystallization plate designs with different dimensions are now in common use. Each crystal must be separated from amorphous precipitates and other crystals that may be sticking to it. The crystal may need to be soaked with solutions containing ligands under investigation or additives that will aid in solving the phases of diffracted X-rays. Normally, the crystal is transferred to a solution containing one or more cryoprotectants, after which the crystal is flash-cooled by plunging it into liquid nitrogen. Every step of the way, care must be taken not to damage the crystal. Choice of soaking and cryoprotectant solutions, as well as soaking time, can affect the quality of the crystal and must be determined by trial-and-error for each type of molecule and each crystal form.

To minimize damage to the crystal, all of these activities must be performed at or close to the temperature at which the crystal was grown. This fact presents a practical dilemma for crystals grown at 4° C. Handling such crystals conventionally requires the experimenter to work in a 4° C. cold room. The experimenter sits motionless in the cold while his fingers do all the work under the microscope. To remain productive, the experimenter often may be required to work in a cold room for extended periods, leading to reduced dexterity as a result of numbness to the hands, even if gloves are worn. The obvious difficulty with this arrangement has discouraged many crystallographers from attempting crystallization at low temperatures, which denies them the ability to obtain crystal structures for a large fraction of chemical space. When low temperature crystallization is undertaken, productivity can be severely limited by the endurance of the experimenter in the cold, and rare is the crystallographer who can routinely work at 4° C. for more than three continuous hours.

SUMMARY OF THE INVENTION

The current invention addresses this inadequacy by allowing the experimenter to work at amenable temperatures while handling crystals maintained at close to 4° C. under the microscope. In essence, this invention provides a large work area under a dissection microscope where the air is cooled by circulation of a transparent liquid of high heat capacity ("coolant"), such as ice water, chilled alcohol, or chilled aqueous ethylene glycol, through walls around the specimen stage and through a transparent chamber beneath the specimen stage, without blocking the light path of the microscope. In one version of this apparatus, circulation of most coolants may be replaced by an array of Peltier coolers (see below). The apparatus is open to the air on top, so that the experimenter has direct access to the crystals for manipulation, but a lid may be used to cover the chamber containing the crystals. To maximize heat exchange efficiency (here, the rate at which the air is cooled around the crystals), parallel fins (composed of a good heat conductor such as copper or aluminum) line the inside walls of the apparatus. The invention may have wider application for manipulation of other specimens under a dissection microscope.

In summary, this invention addresses a shortcoming in current technologies for crystal handling in the field of X-ray crystallography. The subject of this invention is an apparatus that allows a crystal to be maintained at a low temperature during observation and manipulation under an optical microscope prior to data collection, even outside of a 4° Celsius cold room. The apparatus differs from a microscope stage cooler in that the apparatus cools and humidifies the air around and above the specimen, not just the surface below the specimen, and this cooling is accomplished without enclosing the entire microscope in a cooled chamber. Also, the apparatus may be used with a dissection microscope and contains a space that can hold a 24-well, 96-well or other multi-well plate, so that crystals in each well may be viewed or manipulated at the controlled temperature. A humid environment may be maintained around the multi-well plate, such as to prevent dehydration of aqueous crystals. The apparatus may have wider applications for observation and manipulation of other specimens under the microscope as well.

DETAILED DESCRIPTION OF THE INVENTION

Overall Superstructure.

Figure 1:
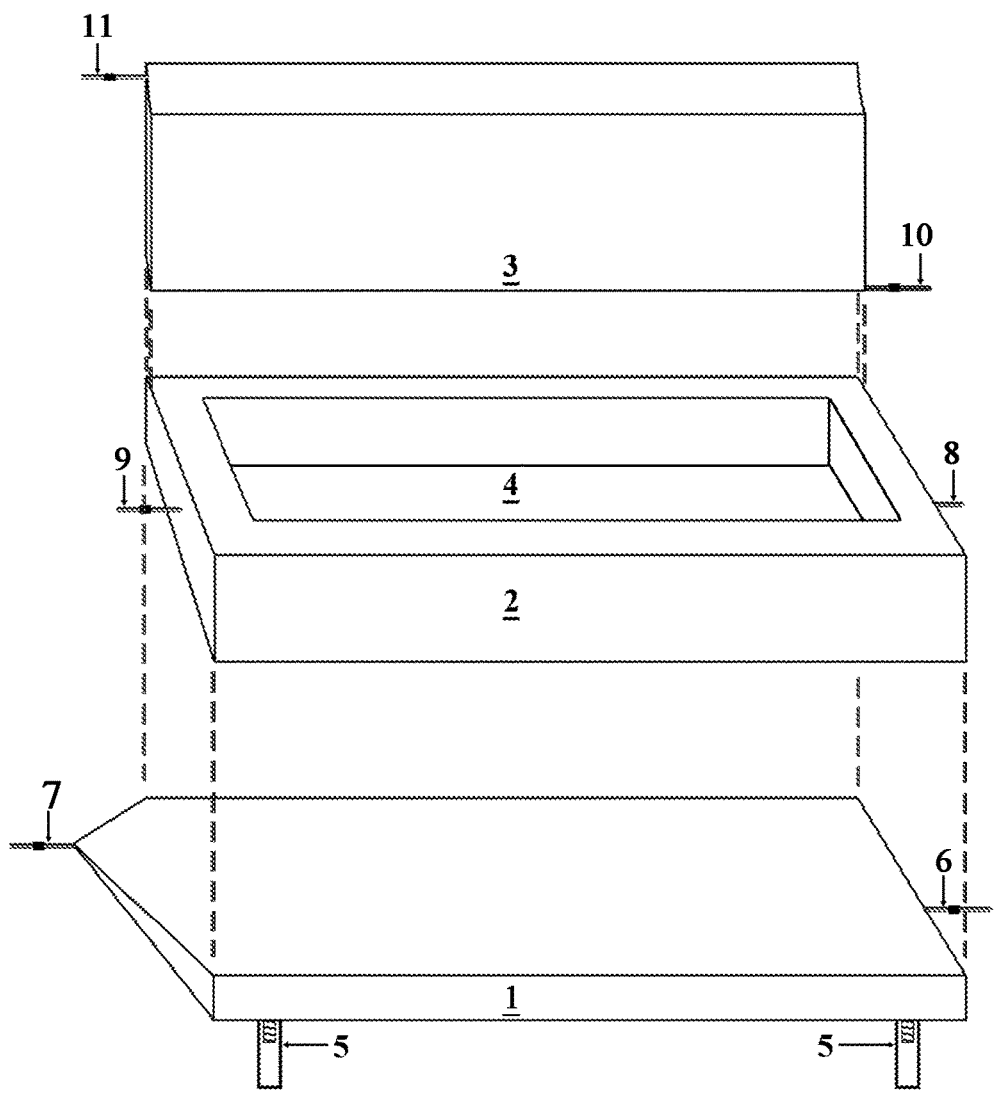
FIG. 1 is an exploded perspective overview of the apparatus according to one embodiment of the invention, stripped of details that are described in subsequent figures.

FIG. 1 shows the overall structure of one embodiment of the present invention, stripped of details that are elucidated in subsequent figures. In its simplest version, the apparatus consists of three stacked chambers termed the Bottom Flow Chamber (1), Lateral Flow Chamber (2), and Exterior Flow Chamber (3). The top and bottom surfaces of the Bottom Flow Chamber are composed of a transparent material (such as plexiglass), but preferably a material that either does not rotate the plane of polarized light or polarizes the plane of light uniformly throughout its area. The Lateral Flow Chamber (2) sits on top of the Bottom Flow Chamber. The Lateral Flow Chamber comprises a hollow wall that partially or completely surrounds a space termed the Specimen Stage Chamber (4). It is in the Specimen Stage Chamber (4) that the experimenter places a vessel containing crystals or other specimens to be viewed (and possibly manipulated) under the microscope. The floor of the Specimen Stage Chamber is formed by the top of the Bottom Flow Chamber (1), while the perimeter of the Specimen Stage Chamber (4) is described by the interior walls of the Lateral Flow Chamber (2). An optional lid can be placed over the top of the Lateral Flow Chamber to isolate the air space of the Specimen Stage Chamber (4) for initial cooling or to protect a specimen. Rising above the rear wall of the Lateral Flow Chamber (2) is the Exterior Flow Chamber (3). Each of these three chambers is supplied with an independent input and output hose connector, and each hose connector is supplied with a valve. The valves give the experimenter control over how to configure the cooling mode. Normally, a coolant is circulated through each of the three chambers, so that the temperature can be controlled for each chamber independently. The Bottom and Lateral Flow Chambers maintain air temperature of the Specimen Stage Chamber (4), while the Exterior Flow Chamber cools ambient air above the rest of the apparatus to create a temperature gradient and induce a gentle passive convection current guiding cool air down toward the Specimen Stage Chamber (4). Additional hose connectors with valves are provided (see "Specimen Stage Chamber", below) that allow the experimenter to pump a fluid or gas directly into the Specimen Stage Chamber to further control temperature and/or humidity around the specimen.

Dimensions and Hose Connector Locations.

All proportions, lengths, or sizes that are stated, implied, or illustrated in the figures and/or this specification are for demonstrative purposes only. The actual apparatus dimensions or shape may be customized for any reason. For example, dimensions may be customized to different microscope models, or the length and/or width of the apparatus may be adjusted, so that the user can shift the position of a given type of crystallization plate from side to side to view each well therein without needing to move this entire apparatus. The figures in this description (and the description in this specification) show all the input hose connectors centered on the right side of the apparatus and all output hose connectors centered on the left, but this invention does not exclude other positions for the hose connectors. Some hose connection configurations are suggested in this specification by way of example, but the actual configuration of hose lines is not the subject of this patent. As indicated below, in some variations of the apparatus, hose connectors may not be required. In the paragraphs below, each of the chambers is described in greater detail.

Bottom Flow Chamber.

Figure 2A:
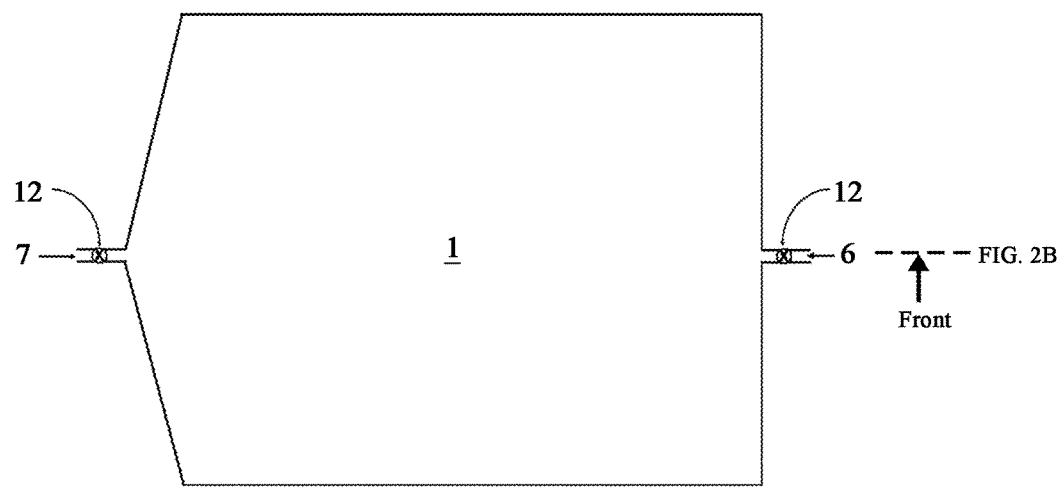
FIG. 2A is a projection view of the Bottom Flow Chamber (1) of FIG. 1, viewed from above.

FIG. 2A is a projection view of the Bottom Flow Chamber (1), viewed from above. The coolant is pumped into hose connector "A-in" (6) and out of hose connector "A-out" (7). The flow of the coolant is controlled by valves (12). Each valve is depicted in this and subsequent figures as a circled X. The size of the hose connectors is not drawn to scale but, rather, is exaggerated for legibility. It is recommended that the hose connectors be centrally positioned between the front and rear to help facilitate laminar flow through the chamber, but this is not a requirement of this patent.

Figure 2B:
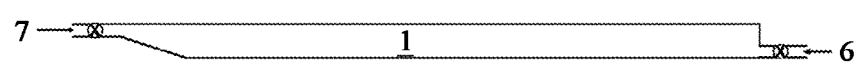
FIG. 2B is a lateral cross-section of the Bottom Flow Chamber (1) of FIG. 1 cut half way between the front and the back.

FIG. 2B shows a lateral cross-section of the Bottom Flow Chamber (1) cut half way between the front and the back. Of note, the "A-in" (6) hose connector is shown positioned as close as possible to the bottom of the chamber, whereas the "A-out" (7) hose connector is shown positioned at the top of the chamber. Moreover, the "A-out" (7) side of the chamber slants up toward the output "A-out" (7) hose connector. These features are designed to help gravity facilitate removal of any bubbles flowing through the coolant, but other chamber shapes or hose connector positions may be used. When crystals grown at 4° C. are manipulated in the apparatus, the lower limit of the coolant temperature should be set at, but not below, 4° C. This is to prevent freezing of the aqueous solution in which crystals often sit during growth and handling. However, crystals or other specimens in non-aqueous or highly concentrated solutions might have different temperature requirements.

The Bottom Flow Chamber (1) may be supported by insertable legs (5) (such as screw-in legs) on the underside of the Bottom Flow Chamber (FIG. 1, 3B) or the optional insulating base block (14 of FIG. 3A) around it. FIGS. 1 and 3B depict a set of legs at the corners of an orthogonally shaped Bottom Flow Chamber, but other arrangements are possible, depending on the microscope model and the shape of the apparatus. The length of the legs is determined so that the entire apparatus sits stably on top of the specimen stage of the microscope. Thus, the open-air crystallization plate cooler should be provided with several sets of accessory legs with lengths tailored to the most common dissection microscopes then in use by crystallographers. The optional base block (14) should be composed of a material that is a poor conductor of heat and may be dark in color to minimize glare and thereby improve optics. The base block (14) should not block the light path of the microscope through the Bottom Flow Chamber (1) and the specimen in the Specimen Stage Chamber (4).

Lateral Flow Chamber.

Figure 3A:
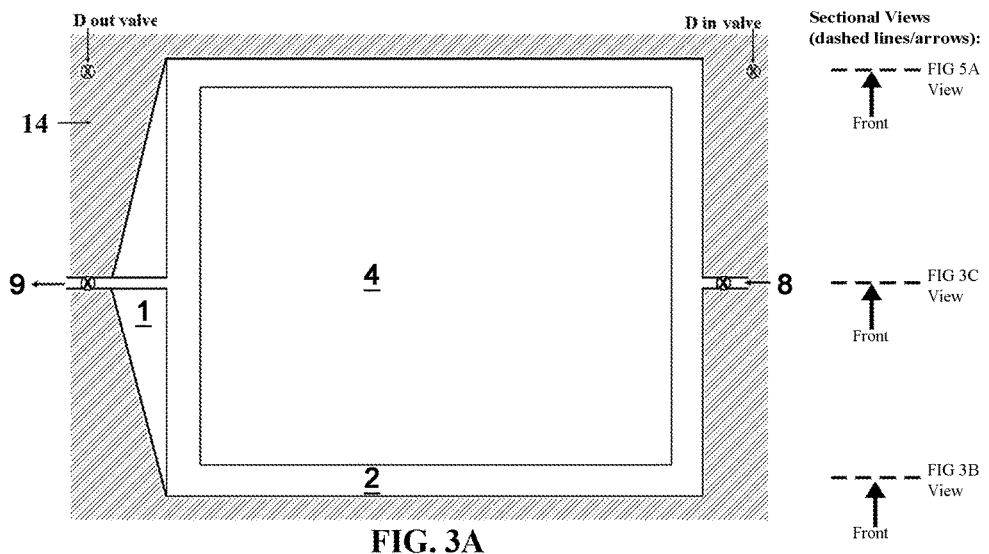
FIG. 3A is a projection view from above the Lateral Flow Chamber (2) and the Specimen Stage Chamber (4) of FIG. 1.
Figure 3B:
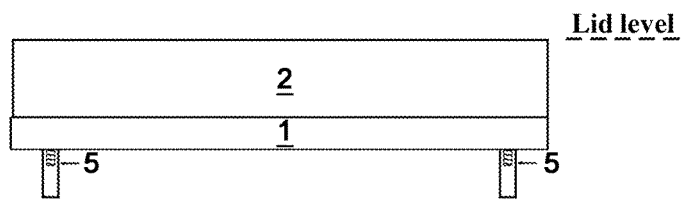
FIG. 3B is a lateral cross-section through the Bottom Flow Chamber (1) and Lateral Flow Chamber (2) of FIG. 1 near the front of the apparatus, viewed from the front.
Figure 3C:
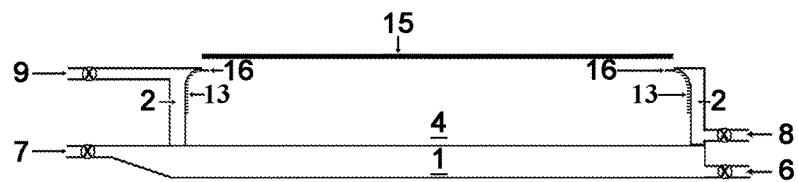
FIG. 3C is a lateral cross-section through the middle of the apparatus of FIG. 1, viewed from the front.

The main features of the Lateral Flow Chamber (2) are depicted in FIG. 3. As in FIG. 2, the size of the hose connectors is not drawn to scale but, rather, is exaggerated for legibility. FIG. 3A shows a projection view from above the Lateral Flow Chamber (2). FIG. 3B shows a lateral cross-section through the Bottom Flow Chamber (1) and Lateral Flow Chamber (2) near the front of the apparatus, and FIG. 3C depicts a cross-section through the middle of the apparatus, all viewed from the front.

The surface area of the Lateral Flow Chamber (2) in contact with the layer of air within the space of the Specimen Stage Chamber (4) may be increased by making the Lateral Flow Chamber (2) slightly wider at the top than for most of its height, so that the top extends or curves over the Specimen Stage Chamber (4). FIG. 3C depicts an example in which the Lateral Flow Chamber (2) has one width at the top and tapers down to half that width for most of the height of the chamber. Some or all of the interior surface of the Lateral Flow Chamber (2) is coated with a material (13) that conducts heat well, such as copper or aluminum (FIG. 3C, 4A, 4B, 4C).

A removable lid (15) fits over an inner lip (16) around the top of the Lateral Flow Chamber (2). This lid should preferably be composed of a transparent material that has the properties of a quarter-wave plate. An inexpensive version of a transparent lid which behaves as a quarter-wave plate would contain a layer composed of a blank (transparent) Polaroid film (or an equivalent material) which is perfectly flat so that it does not distort the image of the specimen viewed through the microscope. The lid should serve as a quarter-wave plate to extend the utility of the apparatus. Alternatively, the lid may be composed of a transparent material that (a) does not rotate the plane of polarized light, or (b) rotates the plane of light uniformly over its entire surface area without distorting the image of the specimen under the microscope. A temperature-controlled coolant is pumped into the Lateral Flow Chamber (2) at "B-in" (8) and out at "B-out" (9), both of which are controlled by valves. Both the "B-in" (8) and "B-out" (9) hose connectors should be centered over the width of the apparatus (FIG. 3A), right above the "A-in" (6) and "A-out" (7) hoses used by the Bottom Flow Chamber (1) (FIG. 3C). For completeness, valves for other hose connectors ["D-in" valve, and "D-out" valve] are shown in FIG. 3A, positioned for ease-of-use in the base block housing the apparatus (14, gray). These additional hoses and valves are explained below. Additional features of the Lateral Flow Chamber (2) are described below under "Heat-conducting Fins".

Specimen Stage Chamber.

Figure 4A:
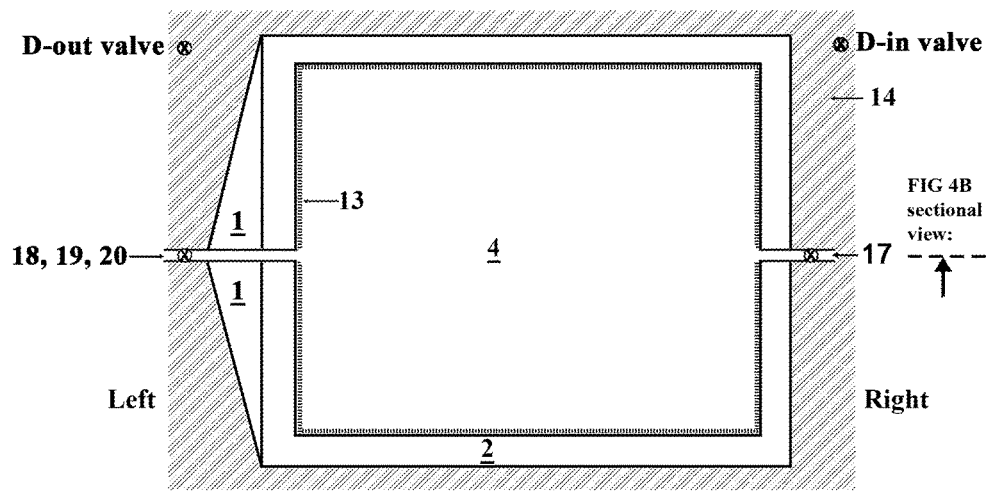
FIG. 4A is a projection view of the Specimen Stage Chamber (4) of FIG. 1 viewed from above, depicting the input and output hose connectors and valves, as well as the metal (or other heat-conducting) coating (13).

The main features of the Specimen Stage Chamber (4) are shown in FIG. 4. FIG. 4A depicts a projection view of the Specimen Stage Chamber (4) viewed from above.

Figure 4B:
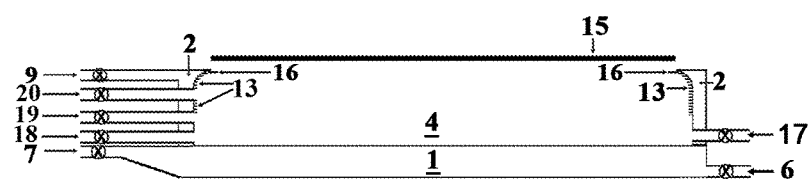
FIG. 4B is a lateral cross-section through the middle of the Specimen Stage Chamber (4) of FIG. 1 to show the suggested relative positions of hose connectors "C-in" (17), "C1-out" (18), "C2-out" (19), and "C3-out" (20).
Figure 4C:
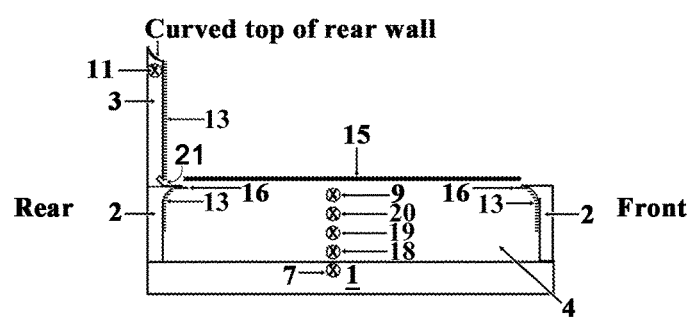
FIG. 4C is a projection view from the left side of the apparatus, including the suggested relative position of the outflow hose connectors and a profile of the suggested shape of the Lateral and External Flow Chambers (2,3) of FIG. 1.

During manipulation of aqueous protein crystals, it is useful to keep the specimen solution in a humid environment to impede the evaporation of solution or the drying out of the protein crystal. For this reason, the Specimen Stage Chamber (4) is supplied with hose connectors to fill the chamber with water (or other liquid or gas) that is optionally cooled by pumping it through a heat exchanger (ice bucket or other cooling arrangement). A vessel containing the specimen (such as a 24-well or 96-well crystallization plate) is placed in this water bath. Water (or other liquid or gas) may be pumped into the Specimen Stage Chamber (4) by way of hose connector "C-in" (17), controlled by a valve. The water leaves the chamber by either hose connector "C1-out" (18), "C2-out" (19), or "C3-out" (20), which are designed to control the level of the water bath. The exact location of the "C-in" hose connector (17) may be determined so as not to interfere with the "B-in" (8) hose connector depicted in FIGS. 3A and 3C. One solution not shown here would be to reverse the direction of fluid flow for the Specimen Stage Center by putting the "C-in" input hose connector (17) on the same side as the "B-out" (9) outflow hose connector of the Lateral Flow Chamber and the outflow hose connectors "C1-out" (18), "C2-out" (19), and "C3-out" (20) on the same side as the "B-in" (8) input hose connector of the Lateral Flow Chamber. FIG. 4B depicts a lateral cross-section through the middle of the Specimen Stage Chamber (4) to show the suggested relative positions of hose connectors "C-in" (17), "C1-out" (18), "C2-out" (19), and "C3-out (20)". FIG. 4C shows a view from the outflow side of the apparatus (the left side in the version depicted by the figure). "C1-out" (18), "C2-out" (19), and "C3-out (20)" hose connectors are situated at different levels above the bottom of the Specimen Stage Chamber (4). They are supplied with valves. The exact height of each of these hose connectors is not the subject of this patent and may be adjusted to accommodate different specimen containers. The exact location of the valve for each hose connector may be located for ease of use. FIG. 4C also depicts the relative location of other outflow hose connectors ["A-out" (7), "B-out" (9), and "D-out" (11)]. The External Flow Chamber (3) and "D-out" (11) are described in detail below.

External Flow Chamber.

Figure 5A:
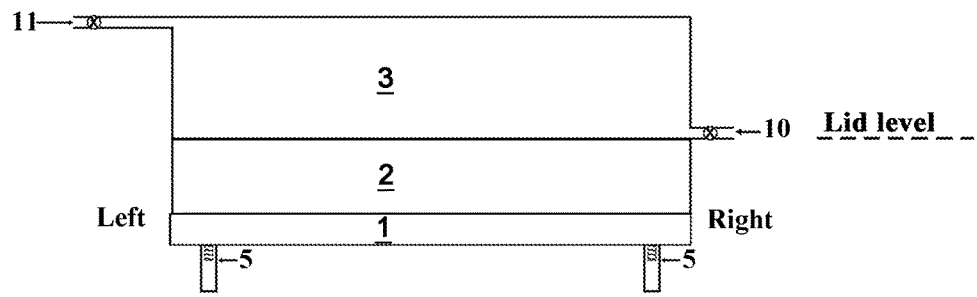
FIG. 5A is a lateral cross-section near the rear of the apparatus of FIG. 1, viewed from the front, showing the stacking of the Bottom, Lateral, and Exterior Flow Chambers (1,2,3) as well as the suggested locations of input hose "D-in" (10) and output hose "D-out" (11).
Figure 5B:
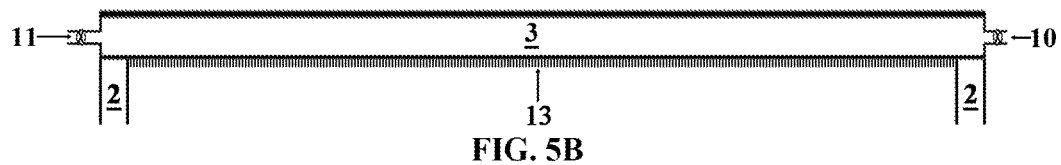
FIG. 5B is an enlarged projection of the External Flow Chamber (3) of FIG. 1, viewed from above, including the suggested locations of the "D-in" (10) and "D-out" (11) hoses.

As introduced above, the External Flow Chamber (3) rises above the rear wall of the Lateral Flow Chamber (2) (FIG. 1) and serves to cool ambient air above the rest of the apparatus, to create a temperature gradient and induce a gentle passive convection current, guiding cool air down toward the Specimen Stage Chamber (4). FIG. 5A shows a lateral cross-section near the rear of the apparatus, and FIG. 5B shows a projection from above. A coolant is pumped into the External Flow Chamber (3) by way of the "D-in" (10) hose connector and out by way of the "D-out" (11) hose connector, one or both of which are controlled by valves. Ideally, the "D-in" (10) hose connector is situated at the bottom of the Lateral Flow Chamber (3), and the "D-out" (11) hose connector is at the top of the chamber. This configuration is designed to help in flushing out bubbles at the top. In addition, this arrangement assures that the coldest temperatures will always be at the bottom of the chamber. The top of the chamber may be curved inward toward the Specimen Stage Chamber (4) to help cooler air to fall toward that chamber (FIG. 4C).

Figure 5C:
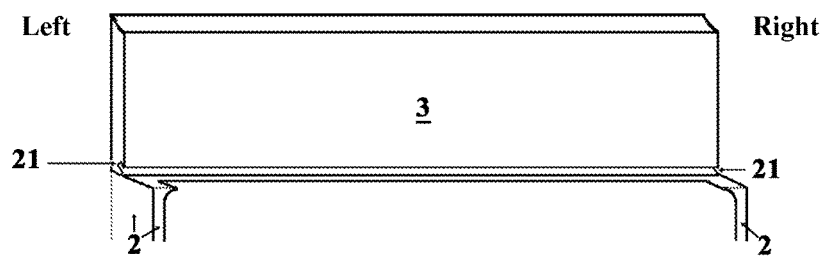
FIG. 5C is a perspective view of part of the apparatus of FIG. 1 just in front of the External Flow Chamber (3) to illustrate the optional notch horizontal air shaft (21) along the underside of the External Flow Chamber (3), viewed from the front.

At part of the underside of the External Flow Chamber (3), facing the top of the Lateral Flow Chamber (2) and Specimen Stage Chamber (4), is an optional notch (21) exposed to the ambient air and stretching horizontally from the right side to the left side of the External Flow Chamber (3) (FIG. 4C, FIG. 5C). The purpose of this horizontal air shaft (which is preferably angled diagonally downward) is to increase cooling surface area of the External Flow Chamber (3) and the volume of cold air sitting right above the Specimen Stage Chamber (4). As air in this shaft cools, it falls towards the Specimen Stage Chamber (4) and gets replaced by relatively warmer ambient air from the sides of the External Flow Chamber (3) by convection. A coating (13) of copper, aluminum, or other heat-conducting material coats the exterior of the inner wall of the External Flow Chamber (3) (including the notched horizontal air shaft (21)) that faces the Specimen Stage Chamber (4) (FIG. 4C, FIG. 5B).

Heat-Conducting Fins.

Figure 6A:
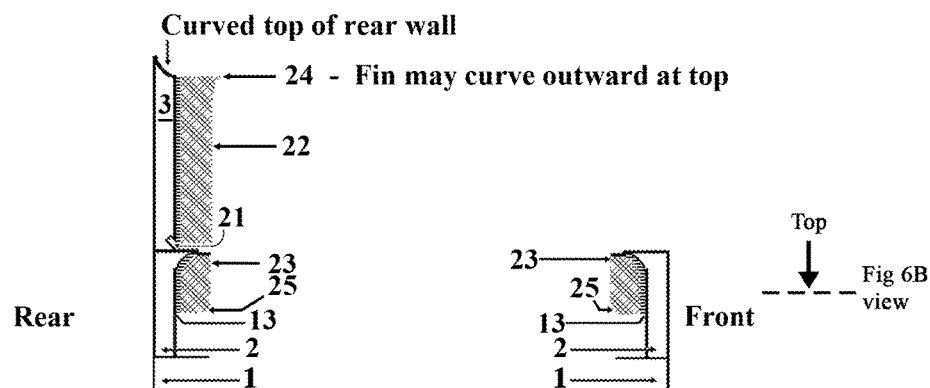
FIG. 6A is a schematic profile of the fins that are positioned vertically on the inner walls of the Lateral and External Flow Chambers (2,3) of FIG. 1 for heat exchange with the air.
Figure 6B:
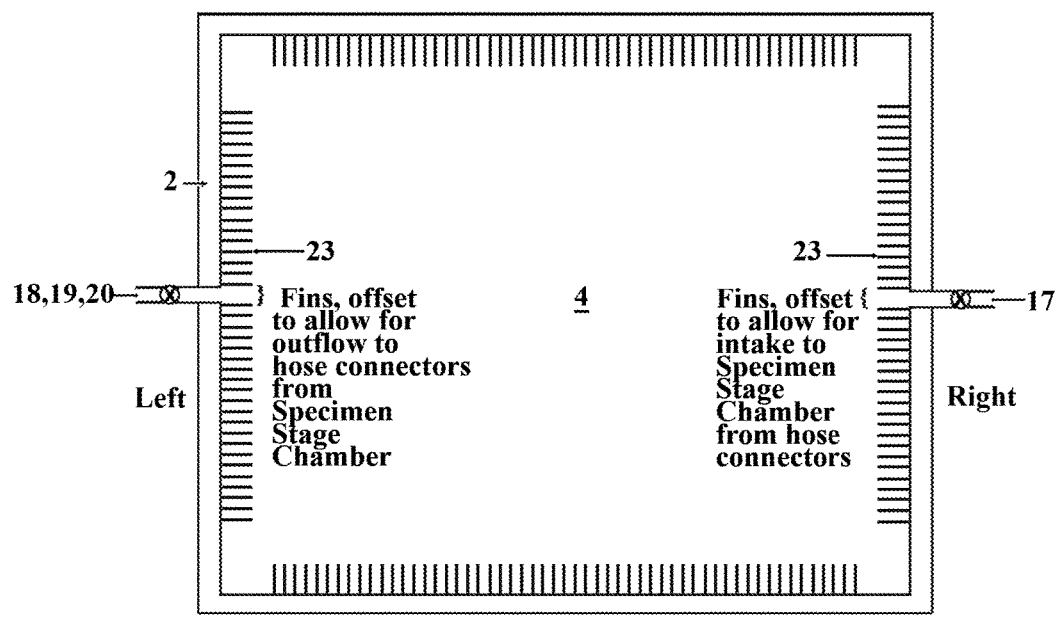
FIG. 6B is a cross-section of the Specimen Stage Chamber (4) of FIG. 1 at about midway above the bottom of the apparatus, viewed from above, showing the position of the heat exchange fins protruding at right angles from the inner walls of the Lateral Flow Chamber (2).
Figure 6C:
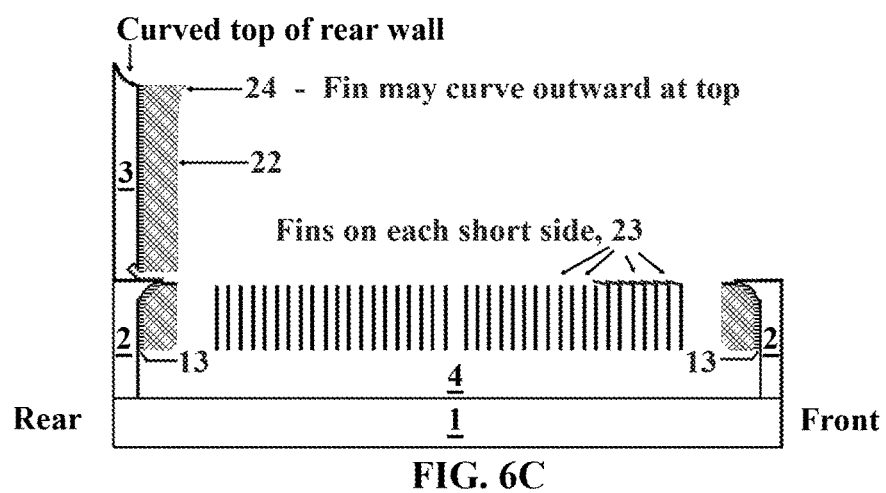
FIG. 6C is a lateral projection of the apparatus of FIG. 1 viewed from the left side, showing the vertical arrangement of heat-conducting fins on the far wall of the Specimen Stage Chamber.
Figure 6D:
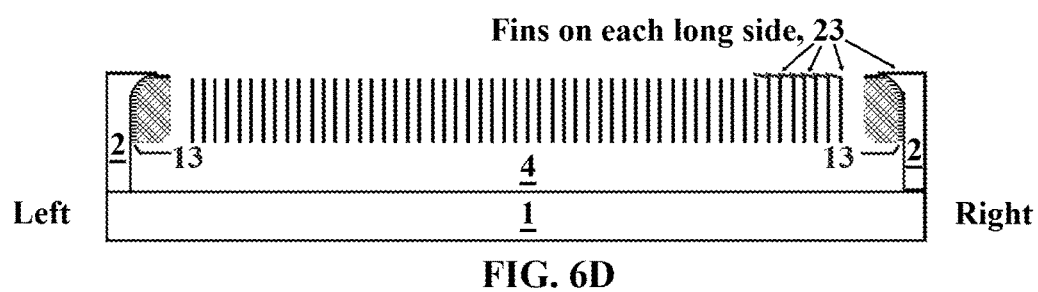
FIG. 6D is a lateral projection of the apparatus of FIG. 1 viewed from the front, showing the vertical arrangement of fins on the far wall of the Specimen Stage Chamber.

To maximize the surface area of heat exchange between the apparatus and the air in (and above) the Specimen Stage Chamber (4), approximately parallel fins of metal (or other heat conductor material) are attached to the wall of the External Flow Chamber (3) and to the wall that the Lateral Flow Chamber (2) shares with the Specimen Stage Chamber, except for the optional notched horizontal air shaft (21). FIG. 6 shows the position of these fins. Each fin is preferably composed of copper, aluminum, or other material with high heat conductance. Each fin (22, 23) protrudes from the inner wall of the Lateral Flow Chamber (2) or External Flow Chamber (3) at approximately a right angle and extends vertically along that wall (FIG. 6A, 6B, 6C, 6D). The top of each External Flow Chamber fin may protrude out (24) to increase its surface area. For example, these fins might protrude out about 2.0 cm at the top and then taper down to 1.5 cm over the majority of the vertical drop of External Flow Chamber. Other arrangements are possible to optimize fin surface area. To increase the working volume in the Specimen Stage Chamber (4) and avoid damage to the fins, the bottom of the fins (25) protruding from the Lateral Flow Chamber (2) may be rounded (FIG. 6A) or otherwise curtailed. Fin positions in the Specimen Stage Chamber (4) may be offset enough so that they do not block intake or outflow hose connectors (FIG. 6B).

Variation 1: Peltier Coolers.

In this optional design variation, Peltier coolers (or other equivalent coolers) replace the Lateral Flow Chamber (2) and External Flow Chamber (3) along with their respective hose connectors and valves. Moreover, the fluid pumped through the Bottom Flow Chamber (1) is passed through an additional Peltier cooler (or other equivalent cooler) as a closed system. Finally, the hoses for the Specimen Stage Chamber are routed through a Peltier cooler (or other equivalent cooler) so that the temperature of the fluid optionally pumped through the chamber can be controlled by the user. All other components of the apparatus (especially the heat-conducting fins) remain in place. This approach can make the apparatus more compact than using multiple hoses and make set-up faster and easier.

Variation 2: Curvature to the External Flow Chamber.

Figure 7A:
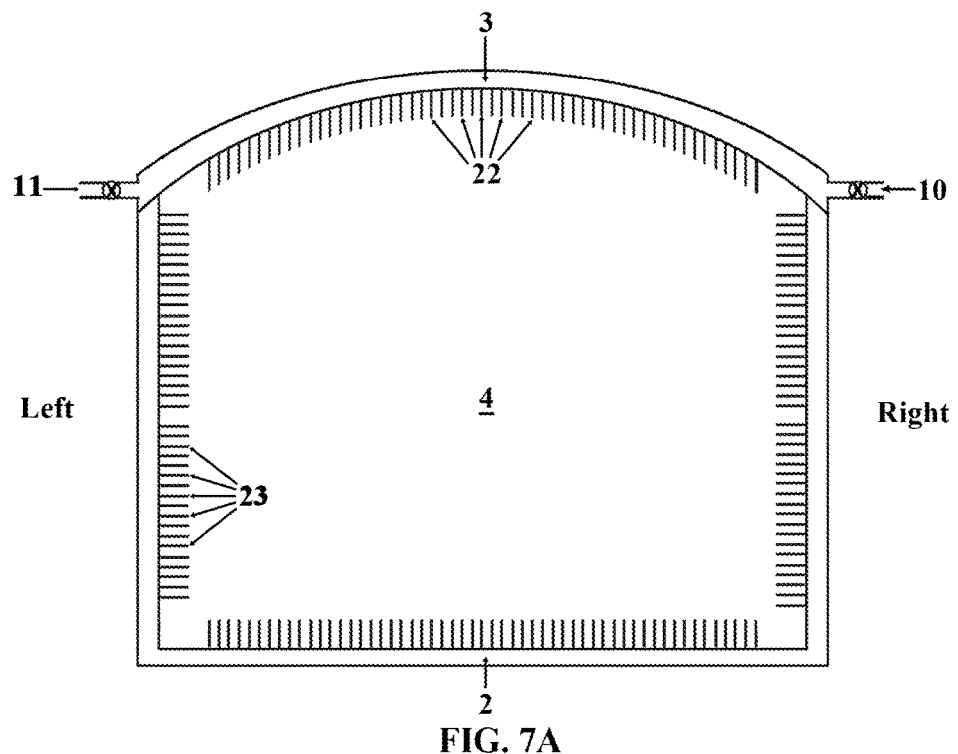
FIG. 7A is a projection from above showing an example of a design variation in which the entire rear wall of the apparatus of FIG. 1 (or at least of the External Flow Chamber) is curved.
Figure 7B:
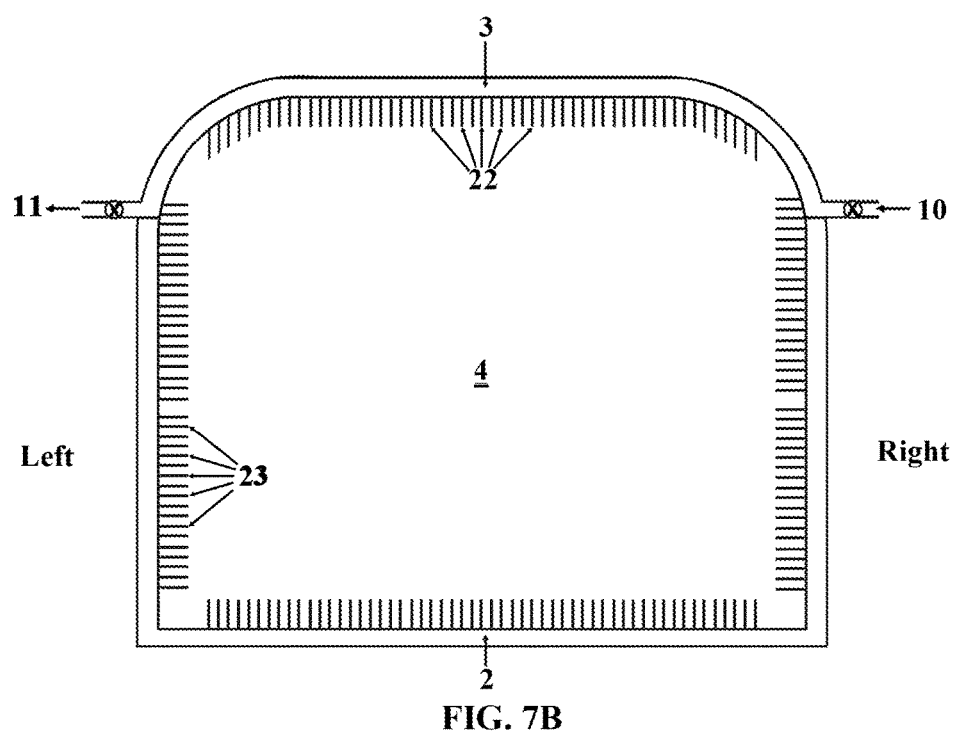
FIG. 7B is a projection from above showing an example of a design variation in which part of the rear wall of the apparatus of FIG. 1 (or at least of the External Flow Chamber) is curved.
Figure 8:
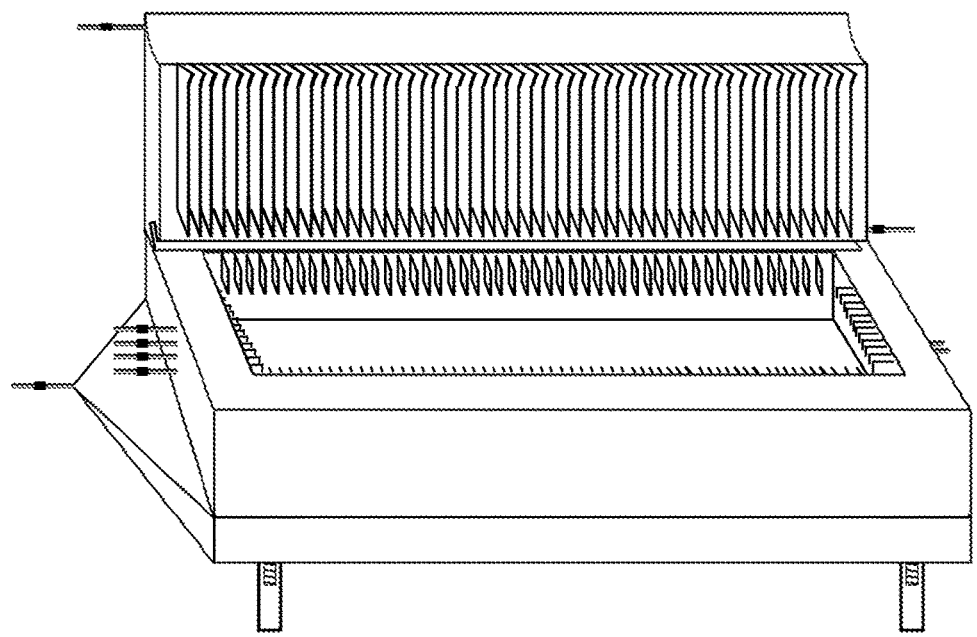
FIG. 8 is a sketch of a version of the entire apparatus of FIG. 1.

In this optional design variation, the External Flow Chamber (3) may be curved concave-in about an imaginary vertical axis (or axes) coming up the interior of the Specimen Stage Chamber (4) in a parabolic, semi-elliptical, circular, or other curved arc (see FIG. 7A for an example of this configuration). Alternatively, most of the External Flow Chamber (3) may be kept orthogonal, with a smaller degree of curvature toward the Specimen Stage Chamber close to the right and left edges of the External Flow Chamber (see FIG. 7B for an example of this configuration). The rear walls of the Lateral Flow Chamber and/or the Bottom Flow Chamber may be curved in like fashion to the External Flow Chamber in order to stack neatly underneath. Introduction of curvature can help to retain cool air above the Specimen Stage Chamber. Other shapes can also be considered in the design. In changing the shape of chambers, the position of the fins on the External Flow Chamber (3) and/or the Lateral Flow Chamber may need to be adjusted or omitted (partially or entirely) to accommodate the curvature or other shape and still allow heat exchange with the ambient atmosphere.

Variation 3: Excluding the Bottom Flow Chamber and/or the Exterior Flow Chamber.

In some cases, it is possible that the Lateral Flow Chamber alone may be adequate for the degree of temperature control that is required, or, for other reasons, the Bottom Flow Chamber and/or the Exterior Flow Chamber may have to be excluded from the apparatus. An example of this might be incompatibility of the full apparatus with the particular geometry or optical properties of a given microscope.

The invention claimed is:

1. An apparatus comprising:
a lateral flow chamber that at least partially surrounds a specimen staging space configured to receive a specimen plate configured to hold one or more specimens; and
at least one of (i) a bottom flow chamber defining a bottom of the specimen staging space and configured to allow light to pass through the bottom flow chamber and (ii) an external flow chamber located on top of at least one side of the lateral flow chamber, wherein:
the apparatus is adapted to be configured with a microscope to enable a user of the microscope to view the one or more specimens held by the specimen plate;

the flow chambers are adapted to control temperature of the one or more specimens held by the specimen plate located within the specimen staging space; and each flow chamber has an input hose connector for receipt of coolant into the flow chamber and an output hose connector for expulsion of the coolant from the flow chamber, wherein at least one hose connector of the input hose connector and the output hose connector has a flow-control valve configured to control flow of the coolant through the at least one hose connector.

2. The apparatus of claim 1, wherein, for at least one flow chamber, the input hose connector is located lower on the flow chamber than the output hose connector.

3. The apparatus of claim 1, wherein, for at least one flow chamber, a corresponding side wall of the chamber slants towards the output hose connector.

4. The apparatus of claim 1, wherein the apparatus comprises the bottom flow chamber.

5. The apparatus of claim 4, wherein the apparatus comprises the external flow chamber.

6. The apparatus of claim 1, wherein the apparatus comprises the external flow chamber.

7. The apparatus of claim 6, wherein the external flow chamber controls temperature of air above the specimen staging space.

8. The apparatus of claim 6, wherein the top of the external flow chamber is curved inward towards the specimen staging space.

9. The apparatus of claim 6, wherein the bottom of the external flow chamber has an air shaft.

10. The apparatus of claim 6, wherein the external flow chamber has a concave curved shape facing towards the specimen staging space.

11. The apparatus of claim 10, wherein at least one of the lateral flow chamber and the bottom flow chamber has a curved side corresponding to the curvature of the external flow chamber.

12. The apparatus of claim 1, wherein the flow chambers are adapted to be independently controlled at different temperatures.

13. The apparatus of claim 1, wherein at least one flow chamber has a plurality of fins extending from a surface of the flow chamber to increase heat exchange between the flow chamber and the ambient environment.

14. The apparatus of claim 1, further comprising a transparent lid adapted to be placed over the specimen staging space, wherein the transparent lid functions as a quarter-wave plate.

15. The apparatus of claim 1, wherein at least one flow chamber is a Peltier cooler.

16. The apparatus of claim 1, wherein the apparatus has an input hose connector having an input flow-control valve for controlling receipt of fluid into the specimen staging space and at least one output hose connector having an output flow-control valve for controlling expulsion of the fluid from the specimen staging space.

17. The apparatus of claim 1, wherein the apparatus is adapted to selectively receive one of two or more different sets of supporting legs of different heights to enable the apparatus to be configured with different types of microscopes.

18. The apparatus of claim 1, wherein at least one side of the lateral flow chamber is wider at the top than at the bottom.

19. The apparatus of claim 18, wherein the wider top of the at least one side of the lateral flow chamber forms an inner lip configured to support a removable lid that is adapted to cover the specimen staging space.

20. The apparatus of claim 1, wherein at least some of the surface of the lateral flow chamber facing the specimen staging space is metallic.

21. The apparatus of claim 1, wherein:
for at least one flow chamber, the input hose connector is located lower on the flow chamber than the output hose connector;
for at least one flow chamber, a corresponding side wall of the chamber slants towards the output hose connector;
the apparatus comprises the bottom flow chamber and the external flow chamber;
the external flow chamber controls temperature of air above the specimen staging space;
the top of the external flow chamber is curved inward towards the specimen staging space;
the bottom of the external flow chamber has an air shaft;
the flow chambers are adapted to be independently controlled at different temperatures;
at least one flow chamber has a plurality of fins extending from a surface of the flow chamber to increase heat exchange between the flow chamber and the ambient environment;
further comprising a transparent lid adapted to be placed over the specimen staging space, wherein the transparent lid functions as a quarter-wave plate;
the apparatus has an input hose connector having an input flow-control valve for controlling receipt of fluid into the specimen staging space and at least one output hose connector having an output flow-control valve for controlling expulsion of the fluid from the specimen staging space;
the apparatus is adapted to selectively receive one of two or more different sets of supporting legs of different heights to enable the apparatus to be configured with different types of microscopes;
at least one side of the lateral flow chamber is wider at the top than at the bottom, the wider top of the at least one side of the lateral flow chamber forming an inner lip configured to support a removable that is adapted to cover the specimen staging space; and
at least some of the surface of the lateral flow chamber facing the specimen staging space is metallic.

22. An apparatus comprising:
a lateral flow chamber that at least partially surrounds a specimen staging space configured to receive a specimen plate configured to hold one or more specimens; and
at least one of (i) a bottom flow chamber defining a bottom of the specimen staging space and configured to allow light to pass through the bottom flow chamber and (ii) an external flow chamber located on top of at least one side of the lateral flow chamber, wherein:
the apparatus is adapted to be configured with a microscope to enable a user of the microscope to view the one or more specimens held by the specimen plate;
the flow chambers are adapted to control temperature of the one or more specimens held by the specimen plate located within the specimen staging space; and
the flow chambers are adapted to be independently controlled at different temperatures.

23. An apparatus comprising:
a lateral flow chamber that at least partially surrounds a specimen staging space configured to receive a specimen plate configured to hold one or more specimens;

at least one of (i) a bottom flow chamber defining a bottom of the specimen staging space and configured to allow light to pass through the bottom flow chamber and (ii) an external flow chamber located on top of at least one side of the lateral flow chamber; and a transparent lid adapted to be placed over the specimen staging space, wherein the transparent lid functions as a quarter-wave plate, wherein:

the apparatus is adapted to be configured with a microscope to enable a user of the microscope to view the one or more specimens held by the specimen plate; and the flow chambers are adapted to control temperature of the one or more specimens held by the specimen plate located within the specimen staging space.

\* \* \* \* \*